(12) United States Patent
Youmans

(10) Patent No.: US 8,332,014 B2
(45) Date of Patent: Dec. 11, 2012

(54) SCANNED BEAM DEVICE AND METHOD USING SAME WHICH MEASURES THE REFLECTANCE OF PATIENT TISSUE

(75) Inventor: David C. Youmans, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 622 days.

(21) Appl. No.: 12/109,799

(22) Filed: Apr. 25, 2008

(65) Prior Publication Data

US 2009/0270724 A1    Oct. 29, 2009

(51) Int. Cl.
*A61B 6/00* (2006.01)
(52) U.S. Cl. .......................... 600/473; 600/476
(58) Field of Classification Search ........... 600/473–480
See application file for complete search history.

(56) References Cited

U.S. PATENT DOCUMENTS

| | | |
|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |

(Continued)

FOREIGN PATENT DOCUMENTS

DE    3837248    5/1990

(Continued)

OTHER PUBLICATIONS

Invitation to Pay Additional Fees with Partial International Search Report, PCT/US2008/074275 (Jan. 16, 2009).

(Continued)

*Primary Examiner* — Sanjay Cattungal
(74) *Attorney, Agent, or Firm* — Thompson Hine L.L.P.

(57) ABSTRACT

Methods for ascertaining, and responding to, a tissue characteristic of a surface region of patient tissue are disclosed. A scanned beam device is used to transmit a beam of sensing radiation to impinge on the surface region and to measure the reflectance of the surface region from the collected radiation returned from the surface region. The tissue characteristic of the surface region is determined from the measured reflectance, wherein the tissue characteristic is different from but related to the measured reflectance. In a first method, an indication of the determined tissue characteristic is provided, wherein the indication is other than a displayed image of the surface region. In a second method, wherein the patient tissue is undergoing medical treatment, the medical treatment is automatically modified as a function of the determined tissue characteristic. A scanned beam device having a scanning beam unit, a collector, and a controller is also disclosed.

21 Claims, 2 Drawing Sheets

U.S. PATENT DOCUMENTS

| | | | |
|---|---|---|---|
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,430,509 A * | 7/1995 | Kobayashi ................. 351/221 |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |

| Patent | Date | Name |
|---|---|---|
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Ono et al. |
| 6,560,028 B2 | 5/2003 | Melville et al. |
| 6,561,648 B2 * | 5/2003 | Thomas ............ 351/221 |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |

| | | | |
|---|---|---|---|
| 2005/0020926 A1 | 1/2005 | Wiklof et al. |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116038 A1 | 6/2005 | Lewis et al. |
| 2005/0162762 A1 | 7/2005 | Novak |
| 2005/0187441 A1 | 8/2005 | Kawasaki et al. |
| 2005/0203343 A1 | 9/2005 | Kang et al. |
| 2005/0240147 A1 | 10/2005 | Makower et al. |
| 2006/0010985 A1 | 1/2006 | Schneider |
| 2006/0084867 A1 | 4/2006 | Tremblay et al. |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0249913 A1* | 10/2007 | Freeman et al. | 600/300 |
| 2007/0260121 A1 | 11/2007 | Bakos et al. |
| 2007/0260273 A1 | 11/2007 | Cropper et al. |
| 2008/0058629 A1* | 3/2008 | Seibel et al. | 600/368 |
| 2009/0231546 A1* | 9/2009 | Dai | 351/246 |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | 98/13720 | 4/1998 |
| WO | 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | 2006/049787 | 5/2006 |
| WO | 2006/055733 | 5/2006 |
| WO | 2007/041542 | 4/2007 |
| WO | 2007/067163 | 6/2007 |
| WO | 2007/070831 | 6/2007 |
| WO | 2007/084915 | 7/2007 |

OTHER PUBLICATIONS

Invitation to Pay Additional Fees with Partial International Search Report, PCT/US2008/074273 (Dec. 30, 2008).
Kiang, M-H et al., "Surface-Micromachined Electrostatic-Comb Driven Scanning Micromirrors for Barcode Scanners" (date of first publication unknown).
Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.com (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PlxBead™ Superior Qualities," http:www.crystalplex.com (date of first publication unknown).
"Microvision [illuminating information] Products/Overview, Corporate Overview Presentation 2006" (2006).
"Holographic Beam Combiner for Ladar, Printer, Fiber Optics, and Cancer Treatment," Optics Technologies, Inc., http://www.mdatechnology.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarzing Cube Beamsplitters," The Engineering Search Engine, http://www.globalspec.com (date of first publication unknown).
Literature entitled "Dallas Semiconductor MAXIM—Visible-Laser Driver has Digitally Controlled Power Modulation," by Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," by Johnson & Johnson, http://www.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
Ra, H. et al., "Biomedical Optics & Medical Imaging—Microtechnology enables endoscopic confocal microscopy," SPIE (http://spie.orb) (2007).
International Search Report issued regarding International Application No. PCT/US2007/078868 (Mar. 28, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
PCT, International Search Report, PCT/US2008/066552 (Oct. 23, 2008).

* cited by examiner

SCANNED BEAM DEVICE AND METHOD USING SAME WHICH MEASURES THE REFLECTANCE OF PATIENT TISSUE

FIELD OF THE INVENTION

The present invention is related generally to scanned beam systems, and more particularly to a scanned beam device, and to a method using a scanned beam device, which measures the reflectance of patient tissue.

BACKGROUND OF THE INVENTION

Conventional scanned light beam systems, such as those adapted to function as bar code scanners, are available from Microvision, Inc. of Redmond, Wash.

An example of an endoscope application of a medical scanned laser beam imager is given in US Patent Application Publication 2005/0020926. The scanned laser beam imager includes a two-dimensional MEMS (micro-electromechanical system) scanner. The MEMS scanner is a dual-resonant-mirror scanner. The mirror scanner scans, about substantially orthogonal first and second axes, one or more light beams (such as light beams from red, green and blue lasers) through an optical dome at high speed in a pattern that traces a trajectory in a two-dimensional acquisition coordinate system. The scanned laser beam imager uses at least one light detector in creating a pixel image from the measured reflectance of the reflected light for display on a monitor.

US Patent Application Publication 2005/0020926 also discloses that light sources having therapeutic properties may be used in the medical scanned laser beam imager for treatment such as a high-powered infrared light source which may be used to cauterize.

What is needed is an improved scanned beam device and an improved method which uses a scanned beam device.

SUMMARY

A first method of the invention is for ascertaining, and responding to, a tissue characteristic of a surface region of patient tissue and includes steps a) through e). Step a) includes obtaining a scanned beam device adapted to transmit a beam of sensing radiation to impinge on the surface region, to collect radiation returned from the surface region which has been impinged with the transmitted beam of sensing radiation, and to measure the reflectance of the surface region from the collected radiation. Step b) includes using the scanned beam device to transmit a beam of sensing radiation to impinge on the surface region. Step c) includes using the scanned beam device to measure the reflectance of the surface region from the collected radiation returned from the surface region. Step d) includes determining the tissue characteristic of the surface region from the measured reflectance, wherein the tissue characteristic is different from but related to the measured reflectance. Step e) includes providing an indication of the determined tissue characteristic, wherein the indication is other than a displayed image of the surface region.

A second method of the invention is for ascertaining, and responding to, a tissue characteristic of a surface region of patient tissue, wherein the patient tissue is undergoing medical treatment, and wherein the second method includes steps a) through e). Step a) includes obtaining a scanned beam device adapted to transmit a beam of sensing radiation to impinge on the surface region, to collect radiation returned from the surface region which has been impinged with the transmitted beam of sensing radiation, and to measure the reflectance of the surface region from the collected radiation. Step b) includes using the scanned beam device to transmit a beam of sensing radiation to impinge on the surface region. Step c) includes using the scanned beam device to measure the reflectance of the surface region from the collected radiation returned from the surface region. Step d) includes determining the tissue characteristic of the surface region from the measured reflectance, wherein the tissue characteristic is different from but related to the measured reflectance. Step e) includes automatically modifying the medical treatment as a function of the determined tissue characteristic.

An embodiment of the invention is for a scanned beam device including a scanning beam unit, a collector, and a controller. The scanning beam unit is adapted to transmit a beam of sensing radiation to impinge on a surface region of patient tissue. The collector is adapted to collect radiation returned from the surface region which has been impinged with the transmitted beam of sensing radiation. The controller is operatively connected to the scanning beam unit and to the collector. The controller is adapted to measure the reflectance of the surface region from the collected radiation and to determine the tissue characteristic of the surface region from the measured reflectance. The controller is also adapted to provide an indication of the determined tissue characteristic, wherein the indication is other than a displayed image of the surface region, and/or to automatically modify an ongoing medical treatment of the patient tissue as a function of the determined tissue characteristic.

Several benefits and advantages are obtained from one or more or all of the methods and the embodiment of the invention. In one example of the first method, a physician is informed by a light bulb or a number display of the completeness of a medical treatment or the presence of a substance in the patient tissue without having the physician study and interpret a sequence of updated images of the patient tissue to make that determination. In one example of the second method, medical treatment is automatically modified without having the physician study and interpret a sequence of images of the patient tissue and act to modify the medical treatment. In one example of the embodiment, a scanned beam device is provided which is adapted to perform the first and/or second methods without the complexity and expense of creating an image from the measured reflectance of the surface region.

DETAILED DESCRIPTION

Before explaining several methods and an embodiment of the present invention in detail, it should be noted that each is not limited in its application or use to the details of construction and arrangement of parts and steps illustrated in the accompanying drawings and description. The illustrative methods and embodiment of the invention may be implemented or incorporated in other methods, embodiments, variations and modifications, and may be practiced or carried out in various ways. Furthermore, unless otherwise indicated, the terms and expressions employed herein have been chosen for the purpose of describing the illustrative methods and embodiment of the present invention for the convenience of the reader and are not for the purpose of limiting the invention.

It is further understood that any one or more of the following-described methods and embodiment and enablements, applications, etc. thereof can be combined with any one or more of the other following-described methods and embodiment and enablements, applications, etc. thereof.

U.S. patent application Ser. No. 11/716,806, entitled MEDICAL DEVICE INCLUDING SCANNED BEAM UNIT FOR IMAGING AND THERAPY, and filed Mar. 12, 2007, is incorporated by reference as if fully set forth herein.

Figure 1:
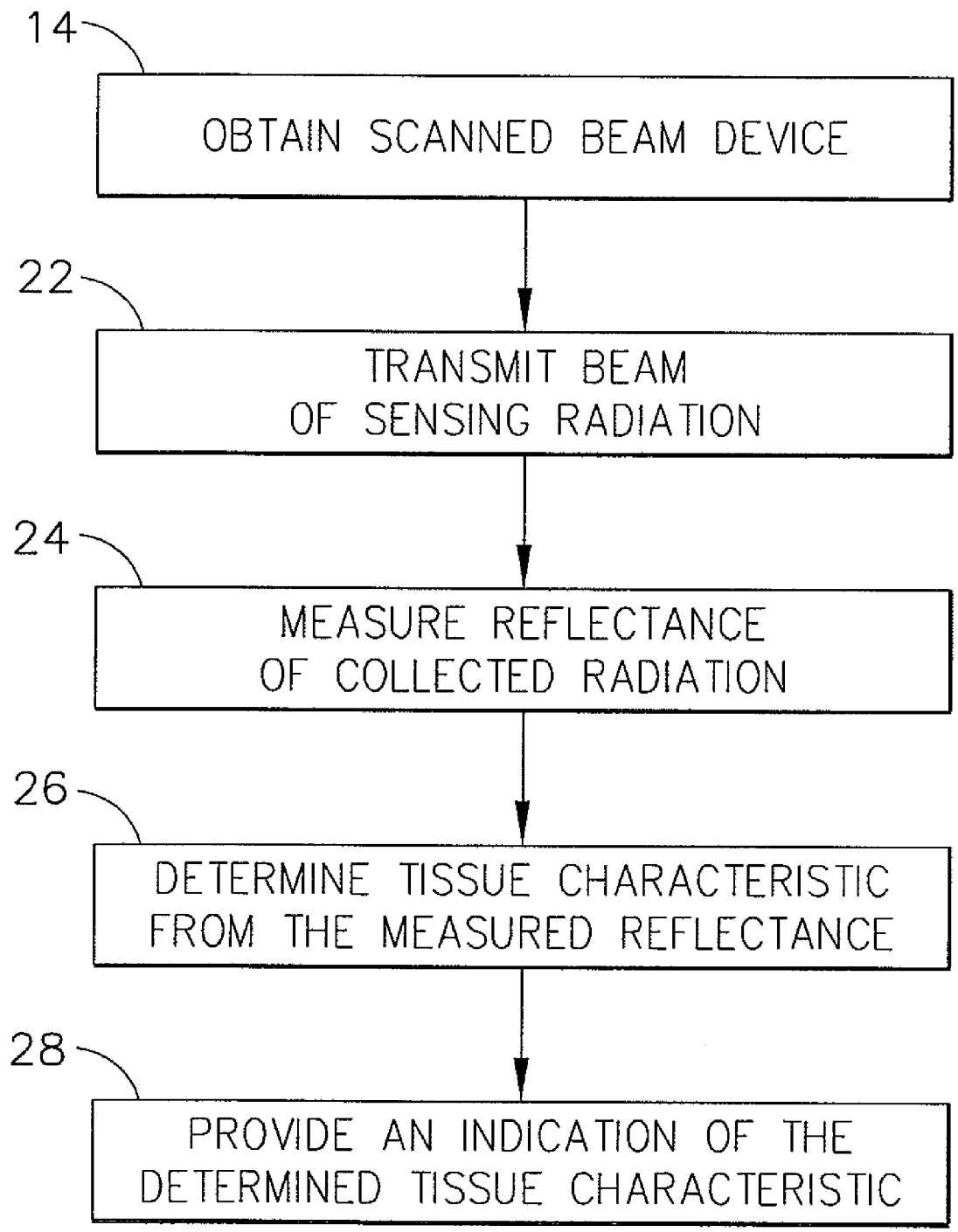
FIG. 1 is a block diagram of a first method of the invention.
Figure 2:
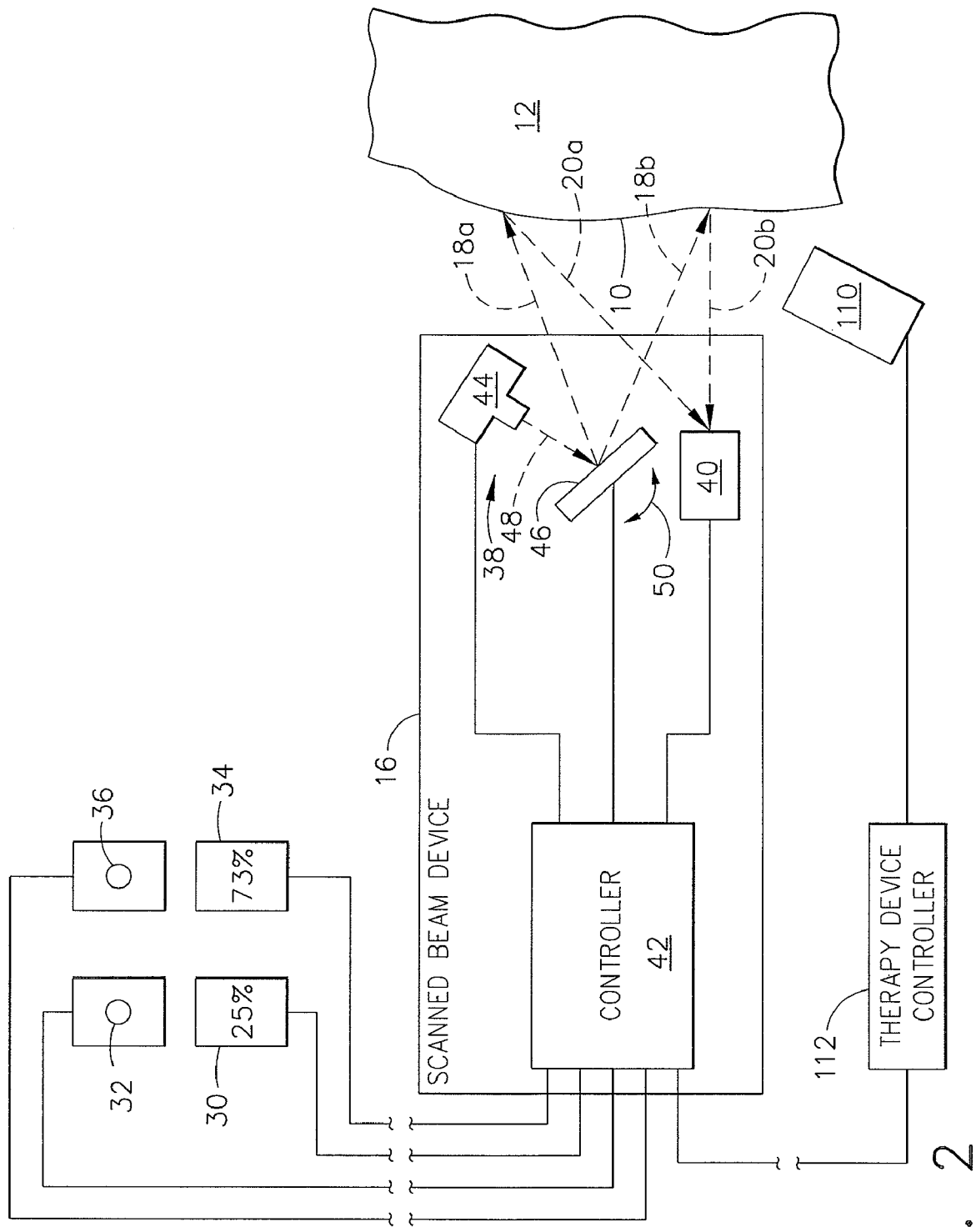
FIG. 2 is a schematic diagram of an embodiment of a scanned beam device which can be used in performing the first method of FIG. 1.

Referring now to the drawings, a first method of the invention is shown in FIG. 1 and an example of an embodiment for carrying out the first method is shown in FIG. 2. The first method is for ascertaining, and responding to, a tissue characteristic of a surface region 10 of patient tissue 12 and includes steps a) through e). Step a) is labeled in box 14 of FIG. 1 as "Obtain Scanned Beam Device". Step a) includes obtaining a scanned beam device 16 adapted to transmit a beam of sensing radiation 18 (shown in two orientations 18a and 18b in FIG. 2) to impinge on the surface region 10, to collect radiation 20 (shown in FIG. 2 as 20a and 20b corresponding to the two orientations 18a and 18b of beam of sensing radiation 18) returned from the surface region 10 which has been impinged with the transmitted beam of sensing radiation 18, and to measure the reflectance of the surface region 10 from the collected radiation 20. Step b) is labeled in box 22 of FIG. 1 as "Transmit Beam of Sensing Radiation". Step b) includes using the scanned beam device 16 to transmit a beam of sensing radiation 18 to impinge on the surface region 10. Step c) is labeled in box 24 of FIG. 1 as "Measure Reflectance of Collected Radiation". Step c) includes using the scanned beam device 16 to measure the reflectance of the surface region 10 from the collected radiation 20 returned from the surface region 10. Step d) is labeled in box 26 of FIG. 1 as "Determine Tissue Characteristic from the Measured Reflectance". Step d) includes determining the tissue characteristic of the surface region 10 from the measured reflectance, wherein the tissue characteristic is different from but related to the measured reflectance. Step e) is labeled in box 28 of FIG. 1 as "Provide an Indication of the Determined Tissue Characteristic". Step e) includes providing an indication of the determined tissue characteristic, wherein the indication is other than a displayed image of the surface region 10.

In one usage of the first method, the patient tissue 12 is internal patient tissue (i.e., tissue within the body of the patient). In this usage, the scanned beam device 16, or at least those portions which transmit the beam of sensing radiation 18 and which collect radiation 20 returned from the surface region 10 are inserted within the patient and disposed proximate the patient tissue 12 of interest. Insertion techniques include, without limitation, using endoscopes, laparoscopes, catheters, open surgery, etc.

In a first enablement of the first method, the tissue characteristic is chosen from the group consisting of a status of a medical treatment of the patient tissue 12 and a status of a presence of a substance in the patient tissue 12.

In a first example of the first enablement, the first method also includes medically treating the patient tissue 12, wherein the tissue characteristic is the status of the medical treatment of the patient tissue 12.

In a first variation of the first example, the status of the medical treatment of the patient tissue 12 is a numerical measure of the completeness of the medical treatment. In one illustration, the providing of the indication includes sending a signal corresponding to the numerical measure to a number display 30. In one modification, the scanned beam device 16 is not adapted to create an image of the surface region 10, and the first method is performed without otherwise creating an image of the surface region 10. If, for some reason, creating an image of the surface region 10 is desired, either the scanned beam device 16 can be adapted to create such image, or a separate imaging device, such as but not limited to an ultrasound imaging probe, may be employed to create such image.

In a second variation of the first example, the status of the medical treatment of the patient tissue 12 indicates whether or not the patient tissue has been fully medically treated. In one illustration, the providing of the indication includes sending (or not sending) a signal which lights or extinguishes a bulb 32 (such as an LED). In one modification, the scanned beam device 16 is not adapted to create an image of the surface region 10, and the first method is performed without otherwise creating an image of the surface region 10.

In one implementation of the first example, medically treating the patient tissue 12 includes ablating the patient tissue 12. In one modification, the scanned beam device 16 is not adapted to medically treat the patient tissue 12, and a separate therapy device 110 and 112 (such as but not limited to a therapy laser unit) having a therapy-device end effector 110 and a therapy-device controller 112 is used to medically treat the patient tissue 12 such as by ablating the patient tissue 12. In a different modification, the scanned beam device 16 is also adapted to transmit a beam of therapy radiation (such as a high power laser beam) to impinge on the surface region 10. Other examples of medical treatment, including coagulation, cauterization, vaporization, desiccation, and photodynamic therapy, are left to those skilled in the art.

In a second example of the first enablement, the tissue characteristic is the status of the presence of the substance in the patient tissue 12.

In a first variation of the second example, the status of the presence of the substance in the patient tissue 12 is a numerical measure of the amount of the substance present. In one illustration, the providing of the indication includes sending a signal corresponding to the numerical measure to a number display 34. In one modification, the scanned beam device 16 is not adapted to create an image of the surface region 10, and the first method is performed without otherwise creating an image of the surface region 10.

In a second variation of the second example, the status of the presence of the substance in the patient tissue 12 indicates whether or not a predetermined amount of the substance is present in the patient tissue 12. In one illustration, the providing of the indication includes sending (or not sending) a signal which lights or extinguishes a bulb 36. In one modification, the scanned beam device 16 is not adapted to create an image of the surface region 10, and the first method is performed without otherwise creating an image of the surface region 10.

In one application of the first method, the beam of sensing radiation 18 has a cross section impinging on the surface region 10, wherein the surface region 10 is larger than the cross section. In this application, the beam of sensing radiation 18 moves over a plurality of different locations on the surface region 10, and the collected radiation 20 is collected from the plurality of the different locations on the surface region 10.

In one arrangement of the first method, the beam of sensing radiation 18 is scanned across a surface area of the patient tissue 12, wherein the surface area is equal to the surface region 10. In a different arrangement, the surface region 10 is a portion, such as a central portion, of the scanned surface area.

In one utilization of the first method, the scanned beam device 16 is implanted within the patient to be aligned with the patient tissue 12 so the beam of sensing radiation 18 will scan the surface region 10 of interest. In one example, the scanned beam device 16 is inserted into a lumen of a patient through a working channel of an endoscope and is attached to the lumen wall by a suture, wherein proper alignment of the scanned beam device 16 with the surface region 10 of interest is obtained from viewing the alignment using the endoscope. It is noted that proper alignment can also be obtained from viewing X-ray or ultrasound, etc. images. In another example, the attachment is by a stent-like, expandable connecting structure. In an additional example, the attachment is by an expandable connecting structure having barbs. Such examples of attachment are disclosed for a scanned beam imager in U.S. patent application Ser. No. 11/651,255 entitled METHOD OF IN VIVO MONITORING USING AN IMAGING SYSTEM INCLUDING SCANNED BEAM IMAGING UNIT, and filed Jan. 9, 2007, and such patent application is incorporated by reference as if fully set forth herein.

In one realization of the first method, the collected radiation 20 for one complete scan of the surface region 10 is sampled along N different locations on the surface region 10, and the measured reflectance for each location is determined. In one illustration, the measured reflectance is updated for each complete scan. In one example, if the measured reflectance at a location is less than a predetermined ablation-complete value or greater than a substance-present value, the location is considered to have been medically treated or the location is considered to have the substance present. If 25% of the locations of the surface region 10 for a complete scan had their measured reflectance correspond to "ablation complete" or "substance present", an indication of the medical treatment of the patient tissue 12 being 25% completed or an indication of the substance being 25% present in the patient tissue 12 would be provided to the number display 30 and 34 or an indication that the medical treatment of the patient tissue 12 was completed or an indication that the substance was present in the patient tissue 12 would not be provided to the light bulb 32 and 36. In this example, if a predetermined percentage (such as, for example, 90%) of the locations had their measured reflectance less than a pre-selected ablation-complete percentage or greater than a pre-selected substance-present percentage, an indication that the medical treatment of the patient tissue 12 is complete (i.e., that the patient tissue has been fully medically treated) or an indication that the substance is present in the patient tissue 12 would be provided to the light bulb 32 and 36.

In a first procedure using the first method, the substance in the patient tissue 12 is a substance naturally occurring in the patient. In a second procedure, the substance is inserted into the patient at a site and travels to the patient tissue 12 of interest. In a third procedure, the substance is a surgical implant, such as a stent, wherein the implant comprises a metal having mirror-like properties, and wherein the tissue characteristic is tissue having a properly attached implant and is determined from a very high measured reflectance of the surface region 10 a predetermined number of days after implanting which indicates that the surgical implant has not moved within the body of the patient.

In one arrangement of the first method, the scanned beam device 16 includes a scanning beam unit 38 which transmits the beam of sensing radiation 18, a collector 40 which receives the collected radiation 20, and a controller 42 operatively connected to the scanning beam unit 38 and to the collector 40. In one example, the scanning beam unit 38 and the collector 40 are adapted to be disposed within the body of the patient. In one variation, the controller 42 includes a memory to store data. In one modification, the controller 42 is also adapted to be disposed within the body of the patient. In a different modification, the controller 42 is adapted to remain outside the body of the patient, such as, but not limited to, the outside-the-body adaptation of the control unit of the scanned beam imager described in the previously incorporated U.S. patent application Ser. No. 11/651,255. In one deployment, the indication of the determined tissue characteristic is provided in real time. In a different deployment, the indication of the determined tissue characteristic is stored and read later.

In a fourth procedure using the first method, a section of the colon of a patient is cut and removed, and the two cut ends of the colon are reattached. The surface region 10 of interest is the area of attachment. The reflectance of the surface region 10 at a specific wavelength is determined a predetermined number of days after the operation. An indication is provided of the tissue characteristic of healthy attached tissue if a measured reflectance higher than a predetermined level was measured days after the operation indicating oxygenated hemoglobin present in the attached tissue. In a fifth procedure, an indication is provided of the tissue characteristic of no blood leaks when a low reflectance at a wavelength corresponding to the color red was measured at a specified time after a surgical procedure indicating the absence of blood. In a sixth procedure, an indication is provided of the tissue characteristic of no bowel leaks when a low reflectance at a wavelength corresponding to the color of fecal matter was measured at a specified time after a surgical procedure indicating the absence of fecal matter. Other procedures are left to those skilled in the art.

In one employment of the first method, the beam of sensing radiation 18 is a beam of visible or invisible (e.g., ultraviolet) light from a low-power laser or from a non-laser source. In one example, the light is white light, wherein the patient tissue 12 has a higher measured white-light reflectance at a location in the surface region 10 when un-ablated and has a lower measured white-light reflectance when ablated. In a different example, light of a specific wavelength impinging on the substance in the surface region 10 of the patient tissue 12 causes the patient tissue 12 to fluoresce at a different specific wavelength, wherein measuring the reflectance of the surface region 10 at the different specific wavelength would result in a lower measured reflectance when the substance was not present and would result in a higher measured reflectance when the substance was present. Examples of radiation beams, other than light beams, are left to those skilled in the art.

A second method of the invention is for ascertaining, and responding to, a tissue characteristic of a surface region 10 of patient tissue 12, wherein the patient tissue 12 is undergoing medical treatment, and wherein the second method includes steps a) through e). Steps a) through d) of the second method are identical to steps a) through d) of the first method previously described. Step e) includes automatically modifying the medical treatment as a function of the determined tissue characteristic. It is noted that "automatically modifying" means modifying without human intervention.

In one enablement of the second method, the tissue characteristic is a status of the medical treatment of the patient tissue 12. In a first example, the status of the medical treatment of the patient tissue 12 is a numerical measure of the completeness of the medical treatment, and the medical treatment is modified to be less intensive as the numerical measure indicates more completeness of the medical treatment of the patient tissue 12. In a second example, the status of the medical treatment of the patient tissue 12 indicates whether or not the patient tissue 12 has been fully medically treated, and the medical treatment is modified by stopping the medical treatment when the status of the medical treatment of the patient tissue 12 indicates that the patient tissue 12 has been fully medically treated. In one implementation, the medical treatment of the patient tissue 12 includes ablating the patient tissue 12.

It is noted that the enablements, implementations, etc. of the first method are equally applicable to the second method.

The following is a list of some of the tissue characteristics which can be determined using the first method and/or the second method of the invention: presence/absence of blood in patient tissue; presence/absence of auto-florescent material in patient tissue; presence/absence of introduced florescent material in patient tissue; presence/absence of necrotized patient tissue; presence/absence of charred patient tissue; presence/absence of reflective material (e.g., a metal stent) in patient tissue; presence/absence of oxygenated hemoglobin in patient tissue; presence/absence of fecal matter or urine in patient tissue; and presence/absence (wherein absence includes elimination and/or conversion) of a photodynamic material (which can be used to shut off therapy).

An embodiment of the invention is for a scanned beam device 16 including a scanning beam unit 38, a collector 40, and a controller 42. The scanning beam unit 38 is adapted to transmit a beam of sensing radiation 18 to impinge on a surface region 10 of patient tissue 12. The collector 40 is adapted to collect radiation 20 returned from the surface region 10 which has been impinged with the transmitted beam of sensing radiation 18. The controller 42 is operatively connected to the scanning beam unit 38 and to the collector 40. The controller 42 is adapted to measure the reflectance of the surface region 10 from the collected radiation 20 and to determine the tissue characteristic of the surface region 10 from the measured reflectance. The controller 42 is also adapted to provide an indication of the determined tissue characteristic, wherein the indication is other than a displayed image of the surface region 10, and/or to automatically modify an ongoing medical treatment of the patient tissue 12 as a function of the determined tissue characteristic.

It is noted that the enablements, implementations, etc. of the first and second methods are equally applicable to the embodiment of the invention.

In one construction of the embodiment of the invention, the scanning beam unit 38 includes a radiation beam source assembly 44 (such as but not limited to a laser assembly) and a reflector 46. The radiation beam source assembly 44 is adapted to emit a beam of radiation 48 toward the surface of the reflector 46. The reflector 46 has substantially orthogonal first and second axes of rotation. The reflector 46 oscillates (note the first oscillation direction 50 in FIG. 2 wherein the second oscillation direction has been omitted for clarity) in a resonant mode about the first and second axes of rotation causing the beam of sensing radiation 18 reflected from the surface of the reflector 46 to trace a trajectory on the surface region 10. The trajectory contains locations corresponding to data samples of the collected radiation 20. In this construction, the collector 40 also acts as a radiation detector and sends the data samples to the controller 42 to be used to measure the reflectance at each of the locations along the trajectory. Other arrangements for receiving the sampled data and other constructions of the radiation beam source assembly are left to the artisan. It is noted that unlabeled solid lines between components in FIG. 2 represent connections between the components and that wireless connections may instead be employed where appropriate. It is also noted that the components of the scanned beam device 16 may or may not be disposed within a single housing.

While the present invention has been illustrated by a description of several methods and an embodiment, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A method for ascertaining, and responding to, a tissue characteristic of a surface region of patient tissue comprising the steps of:
   a) obtaining a scanned beam device including a scanning beam unit, a collector, and a controller wherein, the scanning beam unit is adapted to transmit a beam of sensing radiation to impinge on the surface region, the collector adapted to collect radiation returned from the surface region which has been impinged with the transmitted beam of sensing radiation, and the controller operatively connected to the scanning beam unit and to the collector, wherein the controller measures the reflectance of the surface region from the collected radiation;
   b) using the scanned beam device, the scanning beam unit to transmits a beam of sensing radiation in a scan pattern to impinge on the surface region;
   c) using the scanned beam device, the collector collects the radiation returned from the surface region, and the controller measures the reflectance of the surface region from the collected radiation returned from the surface region;
   d) using the scanned beam device, the controller determines the tissue characteristic of the surface region from the measured reflectance, wherein the tissue characteristic is different from but related to the measured reflectance;
   e) providing an indication of the determined tissue characteristic using the controller, wherein the indication is other than a displayed image of the surface region; and
   f) as a function of the controller automatically modifying the treatment of the determined tissue characteristic.

2. The method of claim 1, wherein the beam of sensing radiation has a cross section impinging on the surface region, wherein the surface region is larger than the cross section, wherein the beam of sensing radiation moves over a plurality of different locations on the surface region, and wherein the collected radiation is collected from the plurality of the different locations on the surface region.

3. The method of claim 1, wherein the tissue characteristic is chosen from the group consisting of a status of a medical treatment of the patient tissue and a status of a presence of a substance in the patient tissue.

4. The method of claim 3, also including medically treating the patient tissue, wherein the tissue characteristic is the status of the medical treatment of the patient tissue.

5. The method of claim 4, wherein the status of the medical treatment of the patient tissue is a numerical measure of the completeness of the medical treatment.

6. The method of claim 5, wherein the providing of the indication includes sending a signal corresponding to the numerical measure to a number display.

7. The method of claim 4, wherein the status of the medical treatment of the patient tissue indicates whether or not the patient tissue has been fully medically treated.

8. The method of claim 7, wherein the providing of the indication includes sending a signal which lights or extinguishes a bulb.

9. The method of claim 4, wherein medically treating the patient tissue includes ablating the patient tissue.

10. The method of claim 3, wherein the tissue characteristic is the status of the presence of the substance in the patient tissue.

11. The method of claim 10, wherein the status of the presence of the substance in the patient tissue is a numerical measure of the amount of the substance present.

12. The method of claim 11, wherein the providing of the indication includes sending a signal corresponding to the numerical measure to a number display.

13. The method of claim 10, wherein the status of the presence of the substance in the patient tissue indicates whether or not a predetermined amount of the substance is present in the patient tissue.

14. The method of claim 13, wherein the providing of the indication includes sending a signal which lights or extinguishes a bulb.

15. A method for ascertaining, and responding to, a tissue characteristic of a surface region of patient tissue, wherein the patient tissue is undergoing medical treatment, comprising the steps of:
   a) obtaining a scanned beam device including a scanning beam unit, a collector, and a controller wherein, the scanning beam unit is adapted to transmit a beam of sensing radiation to impinge on the surface region, the collector adapted to collect radiation returned from the surface region which has been impinged with the transmitted beam of sensing radiation, and the controller operatively connected to the scanning beam unit and to the collector, wherein the controller to measures the reflectance of the surface region from the collected radiation;
   b) using the scanned beam device, the scanning beam unit transmits a beam of sensing radiation in a scan pattern to impinge on the surface region;
   c) using the scanned beam device, the collector collects the radiation returned from the surface region, and the controller measures the reflectance of the surface region from the collected radiation returned from the surface region;
   d) using the scanned beam device, the controller determines the tissue characteristic of the surface region from the measured reflectance, wherein the tissue characteristic is different from but related to the measured reflectance;
   e) providing an indication of the determined tissue characteristic using the controller, wherein the indication is other than a displayed image of the surface region; and
   f) automatically modifying the medical treatment as a function of the determined tissue characteristic.

16. The method of claim 15, wherein the tissue characteristic is a status of the medical treatment of the patient tissue.

17. The method of claim 16, wherein the status of the medical treatment of the patient tissue is a numerical measure of the completeness of the medical treatment, and wherein the medical treatment is modified to be less intensive as the numerical measure indicates more completeness of the medical treatment of the patient tissue.

18. The method of claim 16, wherein the status of the medical treatment of the patient tissue indicates whether or not the patient tissue has been fully medically treated, and wherein the medical treatment is modified by stopping the medical treatment when the status of the medical treatment of the patient tissue indicates that the patient tissue has been fully medically treated.

19. The method of claim 15, wherein the medical treatment of the patient tissue includes ablating the patient tissue.

20. A scanned beam device comprising:
   a) a scanning beam unit adapted to transmit a beam of sensing radiation in a scan pattern to impinge on a surface region of patient tissue;
   b) a collector adapted to collect radiation returned from the surface region which has been impinged with the transmitted beam of sensing radiation; and
   c) a controller operatively connected to the scanning beam unit and to the collector, wherein the controller is adapted:
      (1) to measure the reflectance of the surface region from the collected radiation;
      (2) to determine the tissue characteristic of the surface region from the measured reflectance; and
      (3)
         (a) providing an indication of the determined tissue characteristic, wherein the indication is other than a displayed image of the surface region; and
         (b) automatically modifying an ongoing medical treatment of the patient tissue as a function of the determined tissue characteristic.

21. The scanned beam device of claim 20, wherein the controller provides an indication and automatically modifies the treatment of the tissue.

* * * * *